United States Patent [19]

Sandhack et al.

[11] 4,025,534

[45] May 24, 1977

[54] CONTINUOUS PROCESS FOR PRODUCING GAMMA-BUTYROLACTONE BY CATALYTIC HYDROGENATION OF MALEIC ANHYDRIDE

[75] Inventors: Lothar Sandhack, Rheurdt; Werner Webers, Orsoy; Georg Michalczyk, Neukirchen-Vluyn; Karl-Heinz Gluzěk, Alpen, all of Germany

[73] Assignee: Deutsche Texaco Aktiengesellschaft, Hamburg, Germany

[22] Filed: Jan. 12, 1976

[21] Appl. No.: 648,332

[30] Foreign Application Priority Data

Jan. 15, 1975 Germany ............................ 2501310

[52] U.S. Cl. ............................ 260/343.6; 252/460
[51] Int. Cl.$^2$ ...................................... C07D 307/32
[58] Field of Search ................................ 260/343.6

[56] References Cited

UNITED STATES PATENTS 3,948,805  4/1976  Michalczyk et al. .............. 252/447

Primary Examiner—Cecilia M. S. Jaisle
Attorney, Agent, or Firm—Thomas H. Whaley; Carl G. Ries; George J. Darsa

[57] ABSTRACT

A continuous process for producing gamma-butyrolactone by hydrogenating maleic anhydride in two stages in the presence of a catalyst composed of cobalt oxide and palladium on a support of silica. The hydrogenation is performed at a hydrogen pressure of 100 to 125 atmospheres and at a temperature of 50° to 100° C. in the first stage and at 190° to 220° C. in the second stage.

12 Claims, No Drawings

CONTINUOUS PROCESS FOR PRODUCING GAMMA-BUTYROLACTONE BY CATALYTIC HYDROGENATION OF MALEIC ANHYDRIDE

BACKGROUND OF THE INVENTION

This invention relates to a process for the catalytic hydrogenation of maleic anhydride in the liquid phase to produce gamma-butyrolactone.

The continuous hydrogenation of dicarboxylic acids and dicarboxylic anhydrides, including maleic anhyride, has been disclosed in German Offenlegungsschrift 1,901,870 where hydrogenation of the anhydride is conducted under pressure in the liquid phase at a temperature of about 180° to 280° C. The process is, however, primarily directed to the formation of tetrahydrofuran. If one wishes to obtain gamma-butyrolactone, the process requires higher hydrogen pressures and the butyrolactone must be quickly separated from the reaction mixture. This process has an additional disadvantage in that considerable amounts of polymeric products are formed. German Auslegeschrift 1,668,348 discloses a process for producing gamma-butyrolactone from maleic anhydride by hydrogenating in two stages with different catalysts. Hydrogenation in the gaseous phase is disclosed under a pressure ranging from 0.1 to 5 kg/cm$^2$ and at temperatures of 180° to 290° C. in the first stage and of 220° to 330° C. in the second stage. As it is operated in the gaseous phase, conversion rate and performance are relatively low in this process.

It is an object of the present invention to provide a continuous process for producing gamma-butyrolactone by hydrogenating maleic anhydride in the liquid phase to provide high yields of gamma-butyrolactone having a high degree of purity.

Other objects and advantages will become apparent from a reading of the following detailed description and examples.

DESCRIPTION OF THE INVENTION

Broadly, this invention contemplates a continuous process for producing gamma-butyrolactone by catalytically hydrogenating maleic anhydride which comprises subjecting said anhydride in the liquid phase to a plural stage hydrogenation operation wherein the catalyst employed in each stage of said plural stage hydrogenation operation is cobalt oxide and palladium on silica, where the first stage of said hydrogenation is conducted at a temperature of about 50° to 100° C. and where the final stage of said hydrogenation is conducted at a temperature of about 190° to 220° C. The process is generally conducted at a hydrogen pressure of about 100 to 125 atmospheres. The plural stage hydrogenation can be conducted in a plurality of hydrogenation reactors in series, as for example two reactors, or a single reactor or column can be employed where the hydrogenation is conducted within zones maintained respectively and sequentially at about 50° to 100° C. and about 190° to 220° C.

In a particularly desirable embodiment, our process for the continuous production of gamma-butyrolactone by the catalytic hydrogenation of maleic anhydride is characterized by performing the hydrogenation in a trickle-column reactor filled with a cobalt catalyst, as described herein, in the form of pellets having a diameter of 2-4 mm, said catalyst having a composition of from 20 to 30 weight percent cobalt oxide from 0.1 to 1.5 weight percent palladium and the balance silica under a hydrogen pressure of 100 to 125 atmospheres and at a temperature of 50° to 100° C. for about the first 35 to 42% of the total catalyst column and at a temperature of 190° to 220° C. for the remaining catalyst column and at a load of 2.0 to 5.0, perferably 3.5 to 4.0, moles of maleic anhydride per liter of catalyst per hour.

It has been found that using the cobalt oxide-palladium-silica catalyst described in copending U.S. Application Ser. No. 583,363, filed June 4, 1975, and assigned to the assignee hereof, in a trickle-column reactor under the above-described conditions high conversions and selectivities of maleic anhydride to gamma-butyrolactone in high purity is obtained. Conversion rates of 90 to 94% are easily achieved and can be maintained over very long periods of time without the catalyst losing its activity nor do the hydrogenating conditions need be intensified. Selectivity amounts to over 9% and the process provides high yield of gamma-butyrolactone. It has been observed that after 1000 operating hours, no reduction in catalyst activity was observed.

In one embodiment, the process of this invention can be expediently carried out in a long, narrow reactor and a reactor of about 5 meters in length and about 2.6 centimeters in diameter has proven expecially suitable. The reactor is filled with catalyst pellets whose diameters are relatively small, i.e. 2-4 mm. The catalyst is composed of about 20 to 30 weight percent cobalt oxide, 0.1 to 1.5 weight percent palladium and the balance silica. A preferred catalyst comprises 23 to 27 weight percent, especially 25 weight percent cobalt oxide and 0.4 to 0.6 weight percent, especially 0.5 weight percent palladium.

The catalyst employed herein is non-pyrophoric and is prepared by impregnating silica support with at least one solution of a decomposable salt of a catalytically active metal, drying the impregnated support, heating the impregnated support in air or in a nitrogen containing environment and decomposing the salt, and activating the catalyst in a hydrogen environment. More specifically, the catalyst is prepared by impregnating a silica support with a cobalt salt solution and drying said cobalt impregnated silica, impregnating said dried cobalt impregnated silica support with palladium and drying the cobalt-palladium impregnated silica, calcining said dried impregnated silica support at a temperature sufficient to decompose the cobalt salt to cobalt oxide, and activating said calcined support at a temperature of 400° to 500° C., preferably 420° to 480° C. in a hydrogen atmosphere.

A highly active cobalt catalyst which is non-pyrophoric, may be obtained if the support is dried after its impregnation with the cobalt salt solution, and is only then impregnated with palladium. However, if the silica support is impregnated simultaneously with the cobalt salt solution and palladium or with one solution after the other without intermediate drying, a catalyst is obtained which is pyrophoric.

Commercially available kieselguhr or commercially available SiO$_2$ in the form of granules or pellets having an average diameter of about 1.5 to 3.5 mm., preferably from 2 to 3 mm. may serve as the SiO$_2$ support. Any such pre-formed SiO$_2$ used should be degassed and dried in vacuo at an elevated temperature before it is impregnated with the cobalt salt solution. Fifteen minutes drying at 80°–90° C. is generally sufficient.

The cobalt salt solution is a solution of a cobalt salt which is decomposable when heated, for example the nitrate, the formate, the acetate or the salt of another volatile organic acid.

The palladium can also be introduced in the form of a solution of a salt which is decomposable by reduction; palladium chloride is the least expensive and is thus the preferred salt. The palladium may also be introduced in the form of palladium on carbon (10% by weight of palladium deposited on 90% by weight of activated carbon) which is then admixed with the supporting material impregnated with cobalt.

In contrast to other processes for converting maleic anhydride to γ-butyrolactone which are conducted in the gaseous phase, the process of our invention is carried out in the liquid phase which is a great advantage with regard to conversion and reactor dimensions. The catalytic process can be conducted in a wide range of solvents inert to the reaction as, for example, aliphatic alcohols such as methanol, ethanol, butanol and higher alcohols; aromatics such as benzene, toluene or xylene; dimethylformamide; and cyclic ethers such as tetrahydrofuran or tetrahydropyran. A particularly preferred solvent for converting maleic anhydride is γ-butyrolactone which is the compound that emerges as the end product of the process and this need not be removed. Whether γ-butyrolactone or another solvent is used in the course of the reaction, the results are the same. In general, the maleic anhydride concentration in the solvent can vary from 25 to 75 weight percent. When γ-butyrolactone is employed as solvent about 50 percent solutions are most convenient. In the instance where γ-butyrolactone is intended to be coverted to tetrahydrofuran in a further stage, the reaction solvent for the maleic anhydride in such a case is preferably tetrahydrofuran.

As described above, the anhydride is preferably used as a 50% solution in gamma-butyrolactone or in tetrahydrofuran if the gamma-butyrolactone obtained by hydrogenation is to be further processed to tetrahydrofuran. The feed is introduced to the first stage or at the top of a trickle-column reactor composed of plural stages. The trickling density may be chosen arbitrarily. In general a high trickling density is preferred. The hydrogen may be introduced simultaneously with or in countercurrent to the maleic anhydride feed. The hydrogen pressure should be about 100 to 125 atmospheres in each stage or at the top of the trickle-column reactor. The pressure difference in the reactor or reactors should be less than about 1 atmosphere.

Essential to the invention and contributing to the high conversion rate and the high selectivity is the fact that the first stage is conducted at a temperature of about 50° to 100° C., preferably 75° to 85° C. and in the final stage at about 190° to 220° C., preferably 204° to 209° C.

The temperatures are low as compared to those applied in the known processes. It is possible to control the temperature, i.e. eliminate the reaction heat without difficulties by adiabatic operation of the reactor and, if necessary, by quenching with the solvent. In addition, in a narrow long reactor and in the case of high trickling density it is possible to extend the major reaction zone by increasing the flow rate of the hydrogen gas passing through the reactor.

The product of the instant process, γ-butyrolactone, has utility as a solvent and as a thinner for paints and lacquers. In addition, γ-butyrolactone is useful as an intermediate in the production of tetrahydrofuran.

In order to more fully illustrate the nature of this invention and the manner of practicing the same, the following examples are presented.

EXAMPLE I

At the top of a trickle-column reactor (5 meters long, 2.6 centimeters in diameter) filled with catalyst pellets having a diameter of 2 to 4 mm., a 50% solution of maleic anhydride in gamma-butyrolactone was introduced. Hydrogen was also injected at the top, under a pressure of 107 atmospheres. The temperature was maintained at 80° C. in the first 2 meters of the catalyst column passed by the maleic anhydride solution, and at 206° C. for the remaining catalyst. For over 1,000 operating hours, the temperature was maintained at 206° C. in the second stage of the catalyst, the hourly space velocity amounted to 3.2 mole gamma-butyrolactone per liter and hour. The results achieved are presented in Table I.

TABLE I

| Results | initially | after 1,000 hours |
|---|---|---|
| Product appearance | colorless | colorless |
| Conversion rate | 92 to 96% | 92 to 96% |
| % gamma-butyrolactone | 90 to 92% | 92 to 94% |
| % butyric acid | approx. 2% | 1.6 to 2.0% |
| % other by-products | approx. 2% | 0.5% |

EXAMPLE II

Example I was repeated except that temperatures outside of the ranges to be maintained according to this invention were employed. In the first stage the temperature was 120°, in the second stage 240° C. Table II reports the results achieved.

TABLE II

| Product appearance: | slightly yellow |
|---|---|
| Conversion rate: | 96 to 99% |
| % gamma-butyrolactone: | 78 to 80% |
| butyric acid: | 6 to 10% |
| other by-products: | 4 to 8% |
| succinic acid anhydride: | 1 to 3% |

EXAMPLE III

Example I was repeated except using a copper chromite catalyst having the following composition: 27.0 weight percent $SiO_2$, 5.6 weight percent $Al_2O_3$, 8.6 weight percent CuO, 21.0 weight percent $Cr_2O_3$, 25.5 weight percent NiO, 11.0 weight percent activated carbon, 0.6 weight percent palladium. By using this catalyst under otherwise practically identical conditions, good conversion rates and selectivities are achieved in the beginning, but after only 290 hours on stream, the catalyst activity decreased considerably. The test results are shown in Table III.

TABLE III

| Results | initially | after 250 hours |
|---|---|---|
| Product appearance | green | yellow |
| Conversion rate | approx. 95% | 85 – 90% |
| % gamma-butyrolactone | 80 – 83 | 74 – 78 |
| % butyric acid | 0.5 – 1.0 | 3.0 – 6.0 |
| % succinic acid anhydride in tetrahydrofuran | 8 – 14 | 4 – 8 |
| % by-products | approx. 0.4 | 1.0 – 1.5 |

We claim:

1. A continuous process for producing gamma-butyrolactone by catalytically hydrogenating maleic anhydride which comprises subjecting said anhydride in the liquid phase to a plural stage hydrogenation operation at a pressure of about 100 to 125 atmospheres and at a liquid hourly space volocity of about 2.0 to 5.0 moles of maleic anhydride per liter of catalyst per hour, wherein the catalyst employed in each stage of said plural stage hydrogenation is cobalt oxide and palladium on silica, wherein said catalyst comprises from about 20 to 30 weight percent cobalt oxide, 0.1 to 1.5 weight percent palladium and the balance silica, where the first stage of said hydrogenation is conducted at a temperature of about 50° to 100° C. and where the final stage of said hydrogenation is conducted at a temperature of about 190° to 220° C.

2. A process according to claim 1 wherein said first stage is conducted at about 75° to 85° C.

3. A process according to claim 1 wherein said final stage is conducted at about 204° to 209° C.

4. A process according to claim 1 wherein said catalyst comprises from about 23 to 27 weight percent cobalt oxide, from 0.4 to 0.6 weight percent palladium on a silica support.

5. A process according to claim 1 wherein said plural stage hydrogenation is conducted in two reactors in series.

6. A process according to claim 1 wherein said plural stage hydrogenation is conducted in a single reactor having a first stage zone maintained at about 50° to 100° C. and a final stage zone maintained at about 190° to 220° C.

7. A process according to claim 1 wherein said plural stage hydrogenation is conducted in a trickle-column reactor and where said catalyst is in the form of pellets having a diameter of about 2 to 4 millimeters.

8. A process according to claim 1 wherein said plural stage hydrogenation is conducted in an inert solvent.

9. A process according to claim 8 wherein said solvent is gamma-butyrolactone.

10. A process according to claim 8 wherein said solvent is tetrahydrofuran.

11. A process according to claim 8 wherein the maleic anhydride concentration in said solvent comprises from 25 to 75 weight percent.

12. A process according to claim 8 wherein the maleic anhydride concentration in said solvent comprises 50 weight percent.

* * * * *